(12) United States Patent
Abrahan et al.

(10) Patent No.: US 6,433,148 B1
(45) Date of Patent: Aug. 13, 2002

(54) MONOCLONAL ANTI-IDIOTYPIC ANTIBODIES (AB2) AND THEIR USES

(75) Inventors: Amparo Emilia Macias Abrahan; Rolando Perez Rodriguez; Teresita Rodriguez Obaya; Mercedes Ramos Zamora; Gumersinda Bombino Lopez; Orlando Pena Marichal, all of Habana (CU)

(73) Assignee: Centro de Immunologia Molecular (CIM) (CU)

( * ) Notice: Subject to any disclaimer, the term of this patent is extended or adjusted under 35 U.S.C. 154(b) by 0 days.

(21) Appl. No.: 08/875,706

(22) PCT Filed: Nov. 18, 1996

(86) PCT No.: PCT/CU96/00003

§ 371 (c)(1),
(2), (4) Date: Nov. 17, 1997

(87) PCT Pub. No.: WO97/19113

PCT Pub. Date: May 29, 1997

(30) Foreign Application Priority Data

Nov. 17, 1995 (CU) .............................................. 122/95

(51) Int. Cl.[7] .......................... C07K 16/00; C12P 21/08
(52) U.S. Cl. .............................. 530/388.1; 530/387.1; 530/387.2; 530/388.15; 530/387.7; 436/548
(58) Field of Search ................................. 435/330, 329; 530/387.5, 387.7, 388.1, 387.1; 424/130.1, 137.1, 138.1, 141.1

(56) References Cited

U.S. PATENT DOCUMENTS 5,817,513 A  * 10/1998  Lopez et al. ................ 435/329

FOREIGN PATENT DOCUMENTS

| EP | 88302566.0 | 3/1988 |
| EP | 94203577.5 | 12/1994 |
| EP | 0 657 471 A1 * | 6/1995 |
| WO | PCT/US90/05229 | 9/1990 |
| WO | PCT/AU94/00522 | 9/1994 |

OTHER PUBLICATIONS

Hybridoma (vol. 14) Nov. 1, 1995 p. 98, Monclonal Antiboides (E1, Anti-GM2 Ganglioside) Mary Ann Liebert, Inc.

* cited by examiner

*Primary Examiner*—Laurie Scheiner
(74) *Attorney, Agent, or Firm*—Lackenbach Siegel

(57) ABSTRACT

The present invention describes the selection and use of antidiotypic monoclonal antibodies.

(AB2) IgG type with the main characteristic of being highly connected to the idiotipic network and recognition of B and T human lymphocytes, which are major participants in the immune response.

According to the previous statement the objective of this invention is to provide antidiotypic monoclonal antibodies IgG type connected to the immune network, able to interact with T and B lymphocytes and able to exert an immunoregulatory effect, irmunostimulation or immunosupression that can be used for immunotherapy of autoimune diseases, infectious diseases and cancer.

1 Claim, 14 Drawing Sheets

RECOGNITION PATTERN OF THE HIGH CONNECTED ANTIIDIOTYPIC HIBRIDOMAS WITH DIFFERENT MONOCLONAL ANTIBODIES

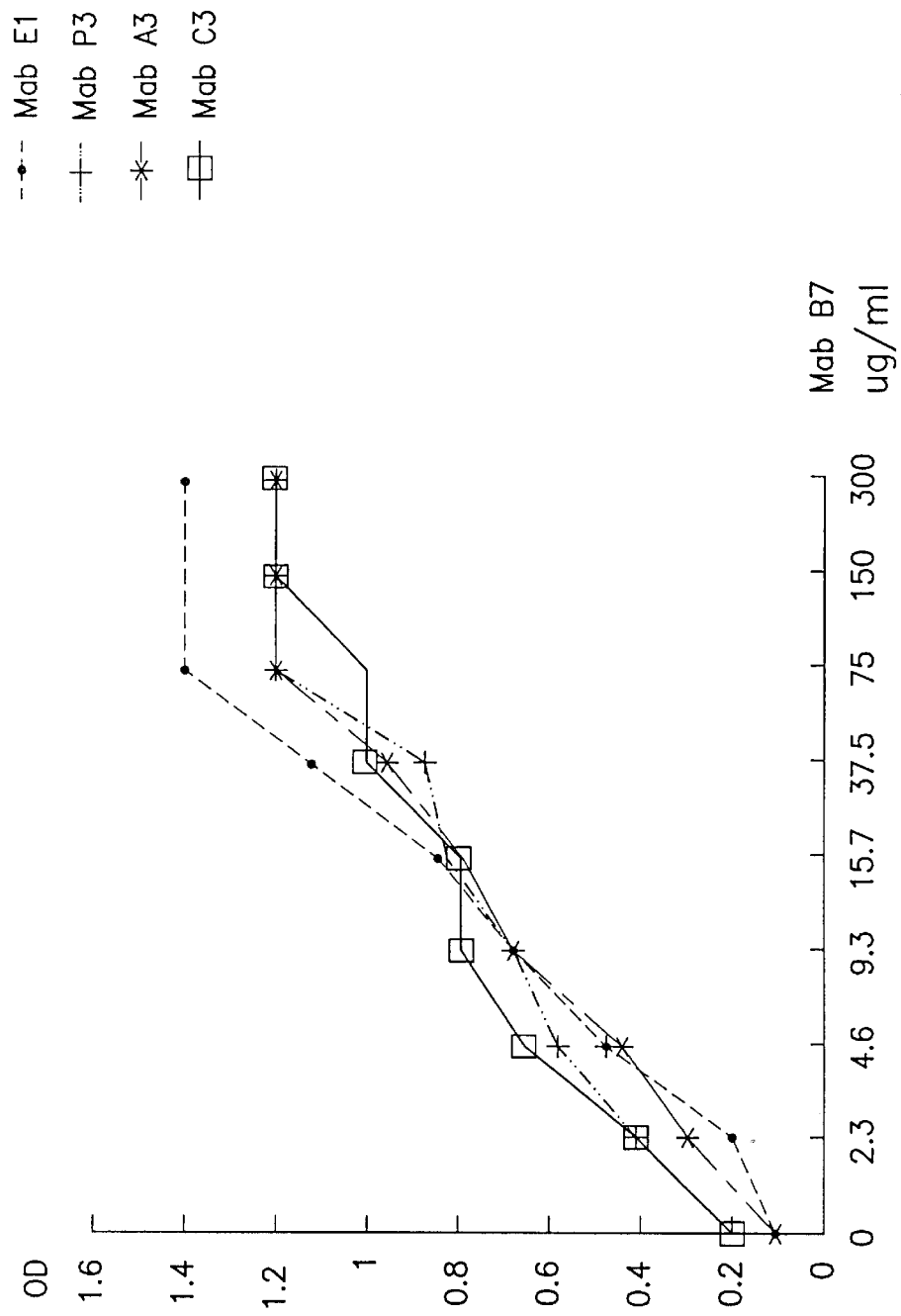

RECOGNITION OF DIFFERENT HUMAN IgG MIELOMA PROTEINS AND THE HUMAN INTRAVENOUS IgG by the B7 Mab BINDING OF DIFFERENT MURINE Mabs BY THE HUMAN MIELOMA PROTEIN #2

RECOGNITION PATTERN OF THE IgG HIGH CONNECTED ANTIIDIOTYPIC Mabs BY DIFFERENT IgG HUMAN MIELOMA PROTEINS BINDING OF UNDIGESTED IgG HUMAN MIELOMA AND THEIR Fab'2 BY THE B7 Mabs COMPETITIVE INHIBITION BY INTRAVENOUS HUMAN IgG OF THE B7 Mab BINDING TO THE HUMAN IgG MIELOMA PROTEIN

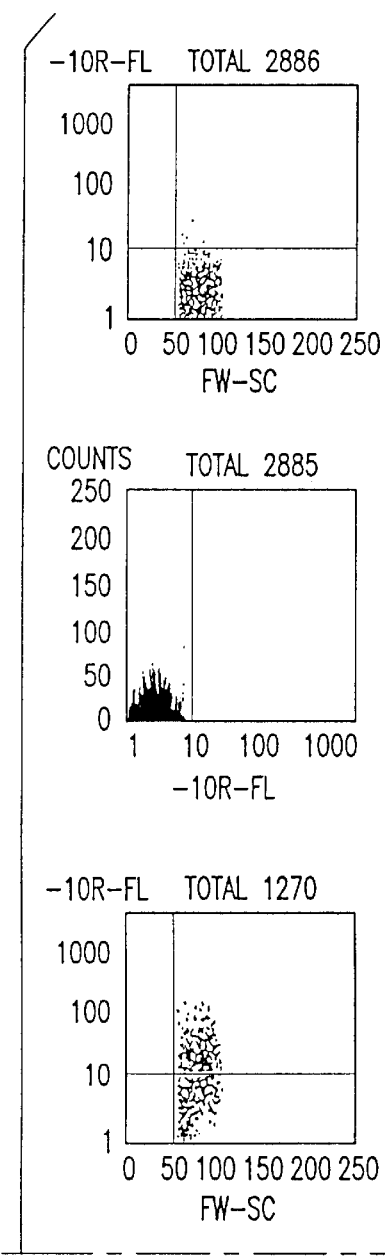

```
GRAPH NUMBER: 2, TUBE:1
GATED BY: A
REG   %TOT   EVENTS   MEAN X   MEAN Y
 −     0.0      0      0.0      0.0
−+     0.0      0      0.0      0.0
+−    98.4   2840     76.9     24.6
++     1.6     45     75.2    107.7
(+*)  100.0  2885
(*+)    1.6    45

GRAPH NUMBER: 3, TUBE:1
GATED BY: A
REG   %TOT   EVENTS   MEAN   PEAK
 1    98.5   2842    24.6      0
 2     1.5     46   108.5     75

REG   SD    CV%
 1   18.2   74.0
 2   38.4   35.4

GRAPH NUMBER: 2, TUBE:1
GATED BY: A
REG   %TOT   EVENTS   MEAN X   MEAN Y
 −     0.0      0      0.0
−+     0.0      0      0.0
+−    51.6    710     76.0     45.0
++    48.4    666     81.9     95.2%
(+*)  100.0  1376
(*+)   48.4   666
```

FIG.8A-1

| FIG.8A-1 |
| FIG.8A-2 |

FIG.8A

FLOW CYTOMETRIC ANALYSIS TO THE PERIPHERAL BLOOD HUMAN LYMPHOCYTES TO DIFFERENT NORMAL HUMAN DONORS BINDING OF B7 Mab TO THE HUMAN LYMPHOCYTES OF DIFFERENT NORMAL HUMAN DONORS (B7 Mab AT 50 ug/ml)

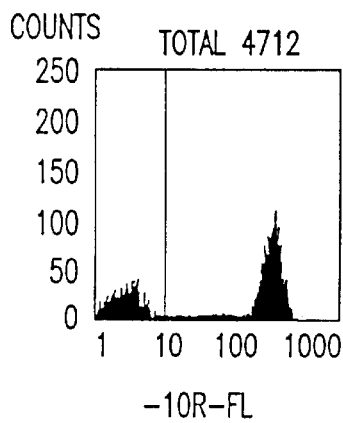

```
                GRAPH NUMBER: 3, TUBE:1
                GATED BY: A
                REG   %TOT    EVENTS    MEAN     PEAK
                 1    40.2    1893      27.8       0
                 2    59.8    2820     181.9     184

REG   SD      CV%
                 1    19.3    69.4
                 2    13.3     7.3
```

FIG.8B

FLOW CYTOMETRIC ANALYSIS TO THE PERIPHERAL BLOOD
HUMAN LYMPHOCYTES TO DIFFERENT NORMAL HUMAN DONORS
POSITIVE CONTROL (CD3 Mab)

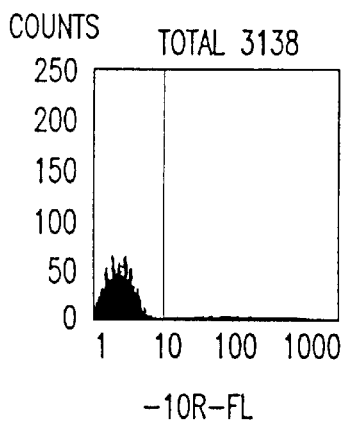

```
                GRAPH NUMBER: 3, TUBE:1
                GATED BY: A
                REG   %TOT    EVENTS    MEAN     PEAK
                 1   100.0    3137      18.4       0
                 2     0.0       1      77.0      77

REG   SD      CV%
                 1    16.1    87.8
                 2     0.0     0.0
```

FIG.8C

FLOW CYTOMETRIC ANALYSIS TO THE PERIPHERAL BLOOD
HUMAN LYMPHOCYTES TO DIFFERENT NORMAL HUMAN DONORS
NEGATIVE CONTROL (R3 Mab)

EFFECT OF THE B7 Mab ON HUMAN LYMPHOCYTES PROLIFERATIVE RESPONSE
HUMAN LYMPHOCYTES + CONA AND PWM

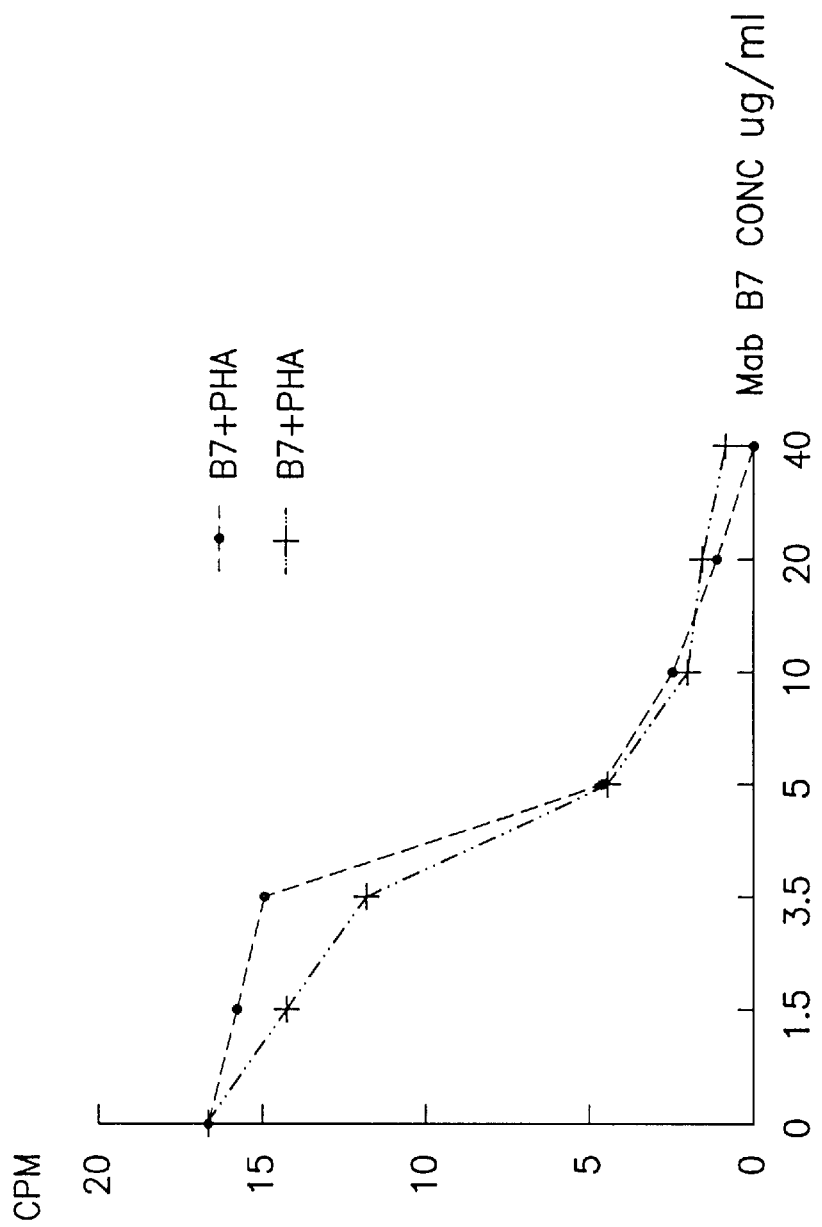

EFFECT OF THE HUMAN INTRAVENOUS IgG
ON HUMAN LYMPHOCYTES PROLIFERATE RESPONSE
iv IgG alone +iv IgG AND CONA EFFECT OF THE HUMAN INTRAVENOUS IgG
ON HUMAN LYMPHOCYTES PROLIFERATE RESPONSE
iv IgG + PHA

| Pos | 1 | 2 | 3 | 4 | 5 | 6 | 7 | 8 | 9 | 10 | 11 | 12 |
|---|---|---|---|---|---|---|---|---|---|---|---|---|
| A | GLN | VAL | GLN | LEU | GLN | GLN | SER | GLY | PRO | GLU | LEU | VAL |
| B | GLN | VAL | GLN | LEU | VAL | GLN | SER | GLY | ALA | GLU | VAL | LYS |
| C | GLN | VAL | GLN | LEU | GLN | GLN | SER | GLY | ALA | GLU | VAL | LYS |

| Pos | 13 | 14 | 15 | 16 | 17 | 18 | 19 | 20 | 21 | 22 | 23 | 24 |
|---|---|---|---|---|---|---|---|---|---|---|---|---|
| A | LYS | PRO | GLY | THR | SER | VAL | LYS | ILE | SER | CYS | LYS | THR |
| B | LYS | PRO | GLY | ALA | SER | VAL | LYS | VAL | SER | CYS | LYS | ALA |
| C | LYS | PRO | GLY | ALA | SER | VAL | LYS | VAL | SER | CYS | LYS | THR |

| Pos | 25 | 26 | 27 | 28 | 29 | 30 | 31 | 32 | 33 | 34 | 35 | 36 |
|---|---|---|---|---|---|---|---|---|---|---|---|---|
| A | SER | GLY | TYR | THR | PHE | THR | GLU | TYR | THR | MET | HIS | TRP |
| B | SER | GLY | TYR | THR | PHE | ALA | GLU | TYR | THR | MET | HIS | TRP |
| C | SER | GLY | TYR | THR | PHE | THR | GLU | TYR | THR | MET | HIS | TRP |

| Pos | 37 | 38 | 39 | 40 | 41 | 42 | 43 | 44 | 45 | 46 | 47 | 48 |
|---|---|---|---|---|---|---|---|---|---|---|---|---|
| A | MET | GLU | GLN | SER | HIS | GLY | LYS | SER | LEU | GLU | TRP | ILE |
| B | VAL | ARG | GLN | ALA | PRO | GLY | GLN | GLY | LEU | GLU | TRP | MET |
| C | VAL | ARG | GLN | ALA | PRO | GLY | GLN | GLY | LEU | GLU | TRP | MET |

| Pos | 49 | 50 | 51 | 52 | 52A | 53 | 54 | 55 | 56 | 57 | 58 | 59 |
|---|---|---|---|---|---|---|---|---|---|---|---|---|
| A | GLY | GLY | VAL | SER | PRO | ASN | ASN | GLY | GLY | ALA | SER | TYR |
| B | GLY | | | | | | | | | | | |
| C | GLY | GLY | VAL | SER | PRO | ASN | ASN | GLY | GLY | ALA | SER | TYR |

| FIG.11A |
|---|
| FIG.11B |

FIG.11 VARIABLE REGION OF THE HEAVY CHAIN OF ANTIBODY B7

FIG.11A

| | 60 | 61 | 62 | 63 | 64 | 65 | 66 | 67 | 68 | 69 | 70 | 71 |
|---|---|---|---|---|---|---|---|---|---|---|---|---|
| A | ASN | GLN | LYS | PHE | LYS | GLY | LYS | ALA | THR | LEU | THR | <u>VAL</u> |
| B | | | | | | | ARG | VAL | THR | MET | THR | <u>ARG</u> |
| C | ASN | GLN | LYS | PHE | LYS | GLY | LYS | ALA | THR | LEU | THR | <u>VAL</u> |

| | 72 | 73 | 74 | 75 | 76 | 77 | 78 | 79 | 80 | 81 | 82 | 82A |
|---|---|---|---|---|---|---|---|---|---|---|---|---|
| A | ASP | LYS | SER | SER | ASN | THR | ALA | TYR | MET | GLU | LEU | 82A |
| B | ASN | GLU | SER | ILE | SER | THR | ALA | TYR | MET | GLU | LEU | ARG |
| C | ASP | LYS | SER | SER | ASN | THR | ALA | TYR | MET | GLU | LEU | SER |
| | | | | | | | | | | | | ARG |

| | 82B | 82C | 83 | 84 | 85 | 86 | 87 | 88 | 89 | 90 | 91 | 92 |
|---|---|---|---|---|---|---|---|---|---|---|---|---|
| A | SER | LEU | THR | SER | ASP | ASP | SER | ALA | VAL | TYR | TYR | CYS |
| B | SER | LEU | ARG | SER | GLU | ASP | THR | ALA | VAL | TYR | TYR | CYS |
| C | SER | LEU | THR | SER | ASP | ASP | SER | ALA | VAL | TYR | TYR | CYS |

| | 93 | 94 | 95 | 96 | 97 | 98 | 99 | 100 | 100A | 100B | 100C | 101 |
|---|---|---|---|---|---|---|---|---|---|---|---|---|
| A | ALA | ARG | ARG | LEU | GLY | ARG | GLY | TYR | ASP | LEU | ALA | SER |
| B | ALA | <u>ARG</u> | | | | | | | | | | |
| C | ALA | ARG | ARG | LEU | GLY | ARG | GLY | TYR | ASP | LEU | ALA | SER |

| | 102 | 103 | 104 | 105 | 106 | 107 | 108 | 109 | 110 | 111 | 112 | 113 |
|---|---|---|---|---|---|---|---|---|---|---|---|---|
| A | TYR | TRP | GLY | GLN | GLY | THR | LEU | SER | ASP | SER | LEU | GLN |
| B | ALA | TRP | GLY | GLN | GLY | THR | LEU | VAL | THR | VAL | SER | SER |
| C | TYR | TRP | GLY | GLN | GLY | THR | LEU | [VAL] | LEU | SER | LEU | GLN |

FIG. 11B

MONOCLONAL ANTI-IDIOTYPIC ANTIBODIES (AB2) AND THEIR USES

FIELD OF THE INVENTION

The present invention is related to the field of Immunology and in particular to the selection and use of antidiotypic monoclonal antibodies (AB2) IgG type with the main characteristic of being highly connected to the idiotipic network and recognition of B and T human lymphocytes, which are major participants in the immune response.

Accordingly the objective of this invention is to provide antidiotypic monoclonal antibodies IgG type connected to the immune network, able to interact with T and B lymphocytes and able to exert an immunoregulatory effect.

DESCRIPTION OF THE PRIOR ART

The immune response is mainly based on the antigen stimulation of some determined B lymphocyte clones bearing in the surface specific receptors for this antigen. T cells have the ability of producing positive and negative signals as a way of regulation of this process. However the immune system regulation mechanisms are very complex as was postulated by Jerne (Jerne N K (1974) Ann Immunol. Inst. Pasteur 125, C:373:389): the immune system can be "seen" as an organized structure of antibody molecules and interconnected lymphocytes by idiotipic directed interactions.

Idiotypes in antibodies are defined as epitopes in the variable regions in such a way each antibody presents particular idiotipical determinants and among them the antigen- antibody recognition region is included. The theory of the idiotipic network emerges from the demonstrated fact (Urbain .J (1976) Ann Immunol. 1231 C; 357) that the idiotipic determinants in the immunoglobulin molecule (AB1) are recognized by antidiotypic antibodies (AB2) obtained against it.

The binding of an idiotypic determinant with its corresponding antidiotypic occurs in a dynamic state that could be perturbed during the course of immune response.

The theory of the idiotypic network proposed by Jerne in the seventies has implicit that the immune repertoire contains and recognize all the possible antigens. Ignoring the dicotomy between self and non sell antigens, thus the existence of autoreactive clones of lymphocytes occurs in a physiological mode.

Studies performed in the last ten years have demonstrated the presence of natural autoreactive antibodies in normal subjects (Avrameas.S., (1991) Immunol. Today, 132C: 231:236, Antin et al (1986), J Immunol. 136,505:510, Lundkvist (1989), PNAS USA 86:5074–5078, Longtenberg .T (1989)J Exp Med, 170:1347.1335)).

These experimental facts have prompted the concept that considers the immune system as a highly connected network of specific receptors ontogenically organized through the internal references (self recognition) philogenetically selected for the maintenance of the homeostatic physiological functions, and more than the normal defense against infections. In this sense recognition of the self is normal and tolerance to the self and memory are not any more considered clone properties as postulates by Burnet in his clone selection theory (Burnet F. M. (1956) London Cambridge University Press) but they are emerging properties of the immune network with an integral point of view (Coutinho, A (1984) Immunol. Rev. 79:151–168, Coutinho. A (1989) Immunol. Rev 110:63–87).

This new concept in relation to the immune system have had its impact in understanding the basic mechanisms of autoimmune diseases and also in the new therapy approach Zanetti. M (1985) Immunol. Today 6: 299–302; Kaveri et al (1991) Clin Exp. Immunol. 96:192–198; Kazatchine. D. M (1994) Immunol. Rev 139:79–107.

An amazing therapeutic effect with different immunoglobulin compounds have observed in the wide variety of systemic and organ specific autoimmune diseases that is useful for the clinical validation of this new concept. (Kazatchine et al (1993) Autoimmunity: physiology and disease Wiley-Liss, Inc., New York).

IgG Immunoglobulin preparations are obtained from blood pools of healthy donors representing the autoreactive physiological network of antibodies. The reactivity analysis in these preparations have demonstrated the existence of antibodies interacting with idiotypes expressed in the autoantibodies and autoantibodies per se (Rossi,et al (1988) Clin Exp. Immunol. 74: 311–316; Rossi et al (1989) J Immunol. 143:4104–4109. Both types of reactivity are in high concentration in the total number of IgG molecules that are more connected than other molecules inside the pool (Dietrich et al (1992) Eur J Immunol. 22:1701–1706). In this way the immunoregulatory effect of these preparations justify the design of new therapeutic strategies addressed to restores the connectivity and diversity in the autoimmune patient. Through this clinical value the concept of emergency of autoimmune disease has been validated, through the fail in the regulatory network in the variable regions of the connected antibodies.

In previous research a panel of monoclonal antibodies against tumor associated gangliosides was obtained, the antigen, classified as T cell independent self antigen EPO: No:0 657 471 A1) These Mabs are IgM type bearing idiotypes able to activate the whole idiotypic network and thus generating an antibody response in absence of the antigen, i.e. they are recurrent idiotypes. These antibodies have been previously described as recognizing specifically the NeucAc GM2 ganglioside (Alfonso. M et al (1995) Hibridoma 14(3): 209–216).

The present invention provides novelty in the generation and selection of a panel of antidiotypic monoclonal antibodies (AB2) against the original IgM antibody recognizing ganglioside.

From this panel a further characterization was performed to one of the antibodies, named B7 showing it was an IgG2a with medium affinity for the antigen (Kd 10 E-8)and alpha type even though this type, it was able to induce an antibody (AB1) independent response in a singeneic model (Balb/C).

Surprising properties have been shown in the antidiotypic antibody B7 studies: High idiotypic connectivity with immunoglobulins of different species human B and T lymphocyte recognition and the immunoregulatory effect on previously activated B and T lymphocytes.

Up to know there isn't any therapy proposing this property in antiidioptype antibodies for the treatment of autoimmune, and infectious diseases and cancer.

The novelty of the present invention consists in the selection of the antidiotypic monoclonal antibodies IgG type highly connected to the immune network through their variable regions able to interact with human B and T lymphocytes and their immunoregulatory effect.

DETAILED DESCRIPTION OF THE INVENTION

GENERATION AND PRODUCTION OF MONOCLONAL ANTIDIOTYPIC ANTIBODIES HIGHLY CONNECTED TO THE IMMUNE NETWORK

For the generation and production of monoclonal antidiotypic antibodies, the Mab against ganglioside is used as immunogen with an immunization procedure is performed as described elsewhere (European Patent Application 657 471 A1).

Mice with high titers of antidiotypic antibodies in serum are reimmunized and three days afterwards the spleen is removed and splenocytes are obtained. Antibody producing cells can be obtained from any other organ if preferred.

These cells are fused with myeloma calls, cell fusion may be performed according to any of the known methods and thus hybridomas are obtained. This method is described in detail in any of the procedures for this purpose.

The antibodies produced are assayed through any immunoassay method preferably an immunoenzimatic method, in which the supernatant are assessed for the presence of specific recognition of the proper antigen. The antibody-antibody binding is detected through a second antibody labeled with an enzyme.

The supernatants are selected for their capacity of blocking the antiganglioside Mab (E1) binding to the antigen (Neu Ac GM2) the supernatants in adequate concentrations are incubated and then the E1 Mab with the antigen.

Once the desired hybridoma has been selected and cloned at least twice by limiting dilution, the resulting Mab can be produced by several culture techniques.

One method can be inoculating the proper amount of cells in the peritoneal cavity of mice producing ascitic fluid in which the Mab is produced in high concentration.

The antidiotypic Mabs obtained recognize different Mabs anti gangliosides related or not related and also are characterized by not blocking the binding of the anti ganglioside Mab to the corresponding antigen.

PROCEDURE FOR THE EVALUATION OF THE IDIOTYPIC CONNECTIVITY IN THE ANTIDIOTYPIC ANTIBODIES (IGG TYPE)

The evaluation of the idiotipic connectivity of antidiotypic monoclonal antibodies of IgG type obtained against the monoclonal antibody antiganglioside E1 recognizing the Neuc Ac GM2 ganglioside is performed using an indirect Immunoenzimatic assay in PVC plates. Plates are coated with specific antigangliosides Mabs and non specific Mabs of murine origin or any other species also human origin Mabs are used for this purpose and IgG pool. The wells are blocked during 1 hour approximately ar room temperature, with PBS and Bovine serum albumin (1%) Followed by the addition of the antidiotypic monoclonal antibodies in a concentration range of 250 ug to 10 ug/mL during two hours in a humid chamber at 37° C. The plate is washed a least 4 times (PBS) and the anti mouse Fc labeled with alkaline Phosphatases conjugate is added during 4 hours. The substrate is added after that time and the plate is read at OD 405 nm.

Negative controls are included, i.e. other antidiotypic monoclonal antibodies not connected to the idiotipic network.

The antidiotypic monoclonal antibodies considered connected recognize the different antibodies coming from different species and their corresponding fragmentsand also recognize the Human pool IgG obtained from human healthy donors, indicating the high connectivity of these Mabs recognizing the idiotypes in the variable regions of immunoglobulins of other species.

PROCEDURE FOR THE EVALUATION OF DIFFERENT SPECIES B AND T LYMPHOCYTE RECOGNITION BY THE ANTIDIOTYPIC MABS (AB2) IGG TYPE IDIOTYPICALLY CONNECTED

The evaluation of the recognition of B and T lymphocytes from different species (mouse, rat monkey and human) by the antidiotypic Mabs(AB2) IgG type idiotypically connected is performed by an Indirect Immunofluorescence assay in a Flow cytometer.

B and T lymphocytes from different species arc isolated by the Ficoll gradient technique from peripheral blood and other lymphoid organs (spleen, lymph nodes and peritoneum) according to the species studied. The cell ring is isolated and the cell counting is done with a Neubauer chamber.

The cell suspension (200 uL) is incubated in a humid chamber during 30 minutes together with the antidiotypic Mab (AB2). Positive controls are added (ior t3 or ior t4) in established conditions and a negative control is also included. A proper conjugate that could be anti mouse FITC or RPE is added and incubated during 30 min. and after that time the sample is measured in the Flow cytometer.

PROCEDURE FOR THE EVALUATION OF THE BIOLOGICAL EFFECT OF ANTIDIOTYPIC MABS (AB2) IGG TYPE IDIOTIPICALLY CONNECTED ON THE B AND T LYMPHOCYTES IN VITRO

For the evaluation of the biological effect of antidiotypic Mabs(AB2) IgG type idiotipically connected on the B and T lymphocytes of any mammal species a cell proliferation assay is performed by 3H-Thimidine incorporation.

The Mononuclear peripheral cells are isolated through a Ficoll gradient technique. The cells in amount of 100000 per well are incubated with the proper medium with 10% serum in microplates. Lymphocyte activators as PHA in a concentration that can be 5 ug/mL, Con A in the same concentration and PWM in the same concentration are added to the incubation in the presence of different concentrations of the antidiotypic Mabs (300 ug to 15 ug/mL).

Controls are included in the assay, activators only, or lymphocyte cells only. Cultures are kept during 72 hours in a 5% CO2 humid atmosphere at 37° C.

3 H-Thymidine is added (1 uCi, 23 uCi/mmol) to each well 6 hours before the culture is arrested. Cells are harvested and 3 H-Thymidine is measured by a beta counter (LKB Sweden).

The highly connected antidiotypic mabs are able to suppress or enhance the stimulation of previously activated B and T lyrphocytes of any species. The antidiotypic Mabs not connected are not able to exert this effect.

PROCEDURE FOR THE EVALUATION OF THE BIOLOGICAL EFFECT OF ANTIDIOTYPIC MABS (AB2) IGG TYPE IDIOTIPICALLY CONNECTED ON THE B AND T LYMPHOCYTES IN VIVO ON DIFFERENT ANIMAL MODELS FOR AUTOIMMUNE DISEASES, INFECTIOUS DISEASES AND MALIGNANT NEOPLASM'S

The in vivo biological effect of Antidiotypic Mabs (AB2) IgG type idiotipically connected on the B and T lymphocytes for autoimmune diseases, infectious diseases and malignant neoplasm's, was measured using differents animals experimental models. The experimental model MRL/1pr/1pr mouse was used to evaluated B7 Mab effects in the autoimmune diseases. This animal develops the Disseminated Lupus Erythematosus (DSL).

MRL/1pr/1pr mice are intraperitoneally injected with high doses of the B7 antidiotypic Mab according to the following scheme: 1 mg/mouse, three times a week, initiating the treatment 24 hours after the birth of the animal and maintaining it during 4 weeks.

Also a low dose regime is evaluated with 100 ug of the antidiotypic Mab at the time of the animal birth.

The therapeutic effect is measured through several aspects: the delayed in time of the clinical signs appearance (skin lesions lymph nodes); through the increase of animal survival and also through the variation of any biological parameter considered as indicator (Proteinuria, anti DNA autoantibodies), A control group of non treated animals was used to establish the comparison.

The evaluation of antitumor effect was performed using an experimental animal model. Mice (C57BL/C) with xenografted lung tumor cells (RL-67) were treated with different doses of the antidiotipic Mab according to the following scheme: 1 mg/mouse, three times a week.

The therapeutic effect is measured through the comparison of survival curves of treated animals versus the control.

The biological effect of the antidiotypic Mabs in infectious diseases was assessed using Balb/C mice previously infected with a clone of Plasmodium Chabaudi.

(Conquy-Adib. M et al (1993) Mol Immunology 30 (2):119–127). After three days of the inoculation the mice were treated with the following therapeutic scheme:

1) A total dose of 800 ug injected in successive doses of 300,100,200, and 200 ug intraperitoneally during one week.

2) A high total doses of 3 mg was administered in 4 weekly injections(two of 1 mg and followed by two of 500 ug) a control group received 0.2 mL of saline solution in the same scheme.

Capacity for delaying the clinical signs appearance is evaluated comparing the control versus the treated group.

PROCEDURE FOR HUMANIZATION AND REDUCE IMMUNOGENICITY OF THE MURINE B7 MONOCLONAL ANTIBODY

B7 Mab was modified in order to decrease its immunogenicity with a procedure (according European patent bulletin #1996/10 under publication no 0699755) which simultaneously reduces immunogenicity of the rodent monoclonal antibody while preserving its binding properties in their entirety. Since the antigenicity of an immunoglobulin is dependent on the presence of T-cell antigenic peptides onto their sequence, the immunogenicity of a xenogenic or allogenic antibody could be reduced by replacing the residues included onto the T-cell antigenic sequences which differ from those usually found in another mammalian species antibodies. Of course, the replacement of residues do not include those involved in to the canonical structures or in the Vernier zone. This judicious replacement of residues have no effect on the structural determinants or on the interdomain contacts, thus, ligand binding properties should be unaffected as a consequence of alterations which are limited to the variable region framework residues.

(1)—Analysis of Homology of Variable Regions.

The present procedure makes use of the available sequence data for human antibody variable domains compiled by Kabat et al., "Sequences of proteins of Immunological Interest" Fifth edition., Bethesda, Md; National Inst. of Health, 1994.

In the first step the variable domains of the murine B7 heavy or light chain are compared with those corresponding variable domains of the human sequences.

The comparison is made by an automated-computerized method (PC-DCS HIBIO PROSIS 06-00, Hitachi.). The most homologous human variable regions are then compared residue for residue to the corresponding murine regions. This will also define the human subgroup to which each mouse sequence most closely resembles.

(2)—Prediction of T-epitopes.

In the second step, the two homologous variable region sequences, mouse and human are analyzed for prediction of T-antigenic sequences.

The algorithm AMPHI (Bersofsky et al., The Journal of Immunology 138: 2213–2229, (1987)) predicts α Helical sequences. The algorithm SOHHA predicts the strip of helix hydrophobicity (Elliott et al., J. Immunol. 138: 2949–2952, (1987)). These algorithms predict T-cell presented fragments of antigenic proteins.

(3) Analysis for Immunogenicity Reduction.

Those residues in the mouse framework which differ from its human counterpart are replaced by the residues present in the human counterpart. This switching occurs only with those residues which are at the T-antigenic sequences.

Finally, replacement of those residues responsible for the canonical structures or those involved in the Vernier zone could have a significant effect on the tertiary structure. Hence, they can not be included in the replacement. Additional information about the influence of the proposed replacements on tertiary structure or the binding site, could be obtained from a molecular model of the variable regions.

(4) The Method for Constructing and Expressing the Altered Antibody.

The following procedures are used to prepare recombinant DNA sequences which incorporate the CDRs of the murine mAb, both light and heavy chains, into human, frameworks that can be used to transfect mammalian cells for the expression of recombinant antibody less immunogenic and with the antigen specificity of the animal monoclonal antibody:

a.-) mutagenesis and assembly of variable region domains including CDRs and FRs regions. The PCR-mutagenesis method (Kamman et al., Nucleic Acids Res. 17: 5404–5409, (1989)) is preferably used to introduce the changes at different positions.

b.-) preparation of an expression vector including one variable region and the corresponding human constant region which upon transfection into cells results in the secretion of protein sufficient for affinity and specificity determinations.

c.-) co-transfection of heavy and light chain expression vectors in appropriate cell lines.

After about 2 weeks, the cell supernatants are analyzed by ELISA for human IgG production. The samples are then analyzed by any method for human IgG capable for binding to specific antigens.

EXAMPLE 1

Generation and Production of Monoclonal Antidiotypic Antibodies (AB2) Highly Connected to the Immune Network Against the E1 Mab Obtained in the Syngeneic Model.

The Mab against ganglioside (E1 Mab) is used as immunogen in Balb/C mice (6–8 weeks old) with an immunization procedure performed as described elsewhere (EP No:0 667 471 A1).

Mice with high titers of antidiotypic antibodies in serum are reimmunized and three days afterwards the spleen is removed and splenocytes are obtained.

These cells are fused with myeloma cells, fusion is performed according to the method described by Kholer and Milstein with some minor modifications (Nature (1975) 256:495–497) and hybridomas are obtained. Murine splenocytes are fused with the non secretor murine myeloma cells P3/X63Ag66.5.3 in a rate 10:1 in 0.5 mL of fusion media containing PEG (3000–5000).

The antibodies produced are assayed through any immunoassay method, in which the supernatants are assessed for the presence of specific recognition of the proper antigen. The antibody-antibody binding is detected through a second antibody labeled with an enzyme.

The supernatants are selected for their capacity of blocking the antiganglioside Mab (E1) binding to the antigen (Neu Ac GM2) the supernatants in adequate concentrations are incubated and then the E1 Mab with the antigen.

The antidiotypic Mabs are selected if they recognized different Mabs anti gangliosides related or not related (FIG. 1) and also they are characterized by not blocking the binding of the anti ganglioside Mab to the corresponding antigen. The hybrid 4B7 was cloned twice and the resultant Mab was the antidiotypic Mab B7 an IgG2a class.

EXAMPLE 2

Procedure for the Evaluation of the Idiotipic Connectivity in the Antidiotypic Antibodies (IgG type).

The evaluation of the idiotipic connectivity of antidiotypic monoclonal antibodies of IgG type obtained against the monoclonal antibody E1 that recognize the Neuc Ac GM2 ganglioside is performed using an indirect Immunoenzimatic assay in PVC plates (96 wells, High Binding Costar). Plates are coated with specific antigangliosides Mabs including the one used as inmunogen the E1 Mab, and non specific Mabs in carbonate-bicarbonate buffer. The wells are blocked during 1 hour at room temperature, with PBS and Bovine serum albumin (1%) Followed by the addition of the antidiotypic monoclonal antibodies in a concentration range of 250 ug to 10 ug/mL during two hours in a humid chamber at 37 ° C. The plate is washed at least 4 times (PBS) and the anti mouse Fc labeled with alkaline Phosphatase conjugate is added during 4 hours. The substrate is added after that time and the plate is read at OD 405 nm.

Negative controls are included, i.e. other antidiotypic monoclonal antibodies not connected to the idiotypic network.

The supernatants of different hydrides producing antidiotypic Mabs recognized the variable regions of the antiganglioside related Mabs, recognized non related IgM of Balb/C origin Mabs, and also neonatal Mabs. (FIG. 1).

The antidiotypic monoclonal antibody B7 IgG2a type showed a high idiotypic connectivity recognizing the idiotypes in the variable regions of the antiganglioside related Mabs, non related IgM of Balb/C origin Mabs, and also neonatal Mabs with an affinity of $10^{-8}$ M.(FIG. 2).

EXAMPLE 3

Characterization of Human Myeloma Immunoglobulin (IgG) Idiotypes Recognition and in the Therapeutic IgG Preparation by the Antidiotypic Mabs Idiotypically Connected.

The capacity of recognition of the human myeloma immunoglobulin (IgG) idiotypes (variable regions) by the B7 Mab was evaluated For this purpose an Indirect Immunoassay is used (96 wells, High Binding Costar). Plates are coated with different IgG fractions or their fragments (obtained according Colligan. E. J et al, Eds (1995) Current Protocols in Immunology). The wells are coated with myeloma proteins in carbonate-bicarbonate buffer and blocked during 1 hour at room temperature, with PBS and Bovine serum albumin (1%) Followed by the addition of the antidiotypic monoclonal antibodies in a concentration range of 380 ug to 11 ug/mL during two hours in a humid chamber at 37° C. The plate is washed at least 4 times (PBS) and the anti goat Fc region labeled with alkaline Phosphates is added and incubated during 4 hours. The substrate is added after that time and the plate is read at OD 405 nm.

The B7 antidiotypic monoclonal antibody recognized the variable regions (idiotypes) present in the human myeloma immunoglobulins (FIG. 3). Other murine Mabs not idiotipically connected did not show any reactivity with this IgG fractions (FIG. 4).

The supernatants of other hydrides producing high connected antidiotypic Mabs recognized the variable regions of the IgG human myeloma proteins. The recognition profile was different for each IgG human myeloma protein.(FIG. 5).

The B7 antidiotypic monoclonal antibody also recognized the variable regions (idiotypes) present in the human myeloma immunoglobulins fragments (FIG. 6).

Moreover the recognition specificity was evaluated through a competence assay for the recognition of the human myeloma IgG by the B7 Mab and different concentrations of the therapeutic human IgG the experiment was performed as followed:

Different concentrations of the therapeutic human IgG were incubated overnight with a fixed concentration of the B7 Mab (95 ug/mL) after that time this mixture was incubated with the human myeloma IgG using the immunoassay already described in this example.

Increasing concentrations of therapeutic human IgG inhibits the B7 Mab recognition for the human myeloma IgG idiotypes. (FIG. 7).

The fact that this B7 Mab of murine origin is able to recognize the variable regions of a human myeloma IgG and the therapeutic human IgG show us the high idiotipic connectivity and suggest that the zones recognized in the variable regions are highly conserved among species.

EXAMPLE 4

Evaluation of Human B and T Lymphocyte Recognition by the Antidiotypic Mabs AB2) IgG Type Idiotipically Connected.

The evaluation of human B and T lymphocytes recognition by the antidiotypic Mabs(AB2) IgG type idiotipically connected is performed by an Indirect Immunofluorescence assay in a Flow cytometer.

B and T lymphocytes are isolated by the Ficoll gradient technique from peripheral blood. The cell ring is isolated and the cell counting is done with a Neubauer chamber. Concentration and cell viability were determined.

The cell suspension (200 uL) adjusted to $10^7$ cells is incubated in a humid chamber during 30 min. together with the antidiotypic Mab (AB2) a standard curve is added in the concentration range of 250 to 10 ug/mL. Positive controls are added (ior t3 or ior t4) in established conditions and a negative control is also included (ior r3). After incubation the wells with the cell suspension are washed with PBS BSA Azide and centrifuging eliminating the supernatant and centrifuge again four times. An anti mouse FITC conjugate is added and incubated during 30 min. in humid chamber and after that the sample is washed and centrifuged again four times, finally the cell suspension is resuspended in 100 uL of PBS and the sample is measured in the Flow cytometer.

FIG. (8A) shows the recognition analysis of human B and T lymphocytes by the B7 Mab in the Flow Cytometer. FIG. (8B) shows the negative control (ior r3 Mab, a non idiotipically connected Mab).

The B7 Mab was able to recognize 53% of human lymphocytes from a normal donor (Peripheral blood lymphocytes). Therefore this Mab of idiotypic reactivity is able to recognize molecular structures present in T and B human lymphocytes.

EXAMPLE 5
Evaluation of the Biological Effect of B37 Antidiotypic Mab (AB2) IgG Type Idiotipically Connected on the B and T Lymphocytes in Vitro.

For the evaluation of the biological effect of B7 antidiotypic Mabs (AB2) IgG type idiotipically connected on the B and T lymphocytes of any mammal species a cell proliferation assay is performed by 3H-Thymidine incorporation.

The peripheral blood lymphocyte cells (PBL) are isolated through a Ficoll gradient technique. The cells in amount of 100000 per well are incubated RPMI 1640 medium with 10% serum in microplates. Lymphocyte activators as PHA in a concentration that can be 5 ug/mL, Con A in the same concentration and PWM in the same concentration are added to the incubation in the presence of different concentrations of the antidiotypic Mabs (300 ug to 15 ug/mL). Controls are included in the assay, activators only, or lymphocyte cells only. Cultures are kept during 72 hours in a 5% CO2 humid atmosphere at 37° C.

3 H-Thymidine is added (1 uCi, 23 uCi/ mmol) to each well 6 hours before the culture is arrested. Cells are harvested and 3 H-Thymidine is measured by a beta counter (LKB Sweden).

The B7 highly connected antidiotypic mab was able to suppress the stimulation of previously activated B and T lymphocytes (FIGS. 9A and B). This suppresser effect of the mytogenic stimulation was also produced by therapeutic human IgG (FIGS. 10A and B) The antidiotypic Mabs not connected are not able to exert this effect.

The fact that this B7 Mab exerts a biological suppresser effect in previously activated B and T human lymphocytes demonstrates the immunoregulator capacity of this highly connected antidiotypic MAB.

EXAMPLE 6
Evaluation of the Biological Effect of Antidiotypic Mabs.

(AB2) IgG type Idiotypically Connected on the B and T Lymphocytes in vivo on Different Animal Models for Autoimmune Diseases, Infectious Diseases and Malignant Neoplasm's.

The in vivo biological effect of antidiotypic Mabs (AB2) IgG type idiotipically connected on the B and T lymphocytes for autoimmune diseases, infectious diseases and malignant neoplasm's, was measured using differents animals experimental models. The experimental model MRL/1pr/1pr mouse was used to evaluated B7 Mab effects in the autoimmune diseases. This animal develops the Disseminated Lupus Erythematosus (DSL).

MRL/1pr/1pr mice are intraperitoneally injected with high doses of the B7 antidiotypic Mab according to the following scheme: 1 mg/mouse, three times a week, initiating the treatment 24 hours after the birth of the animal and maintaining it during 4 weeks.

Also a low dose regime is evaluated with 100 ug of the antidiotypic Mab at the time of the animal birth.

The therapeutic effect is measured through several aspects: the delayed in time of the clinical signs appearance (skin lesions lymph nodes); through the increase of animal survival and also through the variation of any biological parameter considered as indicator (Proteinuria, anti DNA autoantibodies). A control group of non treated animals was used to establish the comparison.

The evaluation of antitumor effect was performed using an experimental animal model. Mice (C57/BL/C) with xenografted lung tumor cells (RL-67) were treated with different doses of the antidiotipic Mab according to the following shim; 1 mg/mouse, three times a week.

The therapeutic effect is measured through the comparison of survival curves of treated animals versus the control.

The biological effect of the antidiotypic Mabs in Infectious diseases was assessed using Balb/C mice previously infected with a clone of Plasmodium Chabaudi (Conquy-Adib.M et al (1993) Mol Immunology 30(2):119–127) After three days of the inoculation the mice were treated with the following therapeutic scheme:

A total dose of 800 ug injected in successive doses of 300, 100, 200, and 200 ug intraperitoneally during one week.

A high total doses of 3 mg was administered in 4 weekly injections (two of 1 mg and followed by two of 500 ug) a control group received 0.2 mL of saline solution in the same scheme.

Capacity for delaying the clinical signs appearance is evaluated comparing the control versus the treated group.

EXAMPLE 7
Pharmaceutical Composition Containing Antidiotypic Monoclonal Antibodies.

A therapeutic composition was obtained containing an effective amount of the antidiotypic monoclonal antibodies highly idiotipically connected and combinations of them, in a pharmaceutical vehicle composed by Dibasic Sodium phosphate 9.0 mg, Monobasic Sodium Phosphate 2.55 mg and Sodium Chloride 43.00 mg, polisorbato 80 1 mg, WFI 5.00 mL. This pharmaceutical composition is to be used in autoimmune diseases, infectious diseases and cancer.

EXAMPLE 8
Murine Variable Region of B7 Monoclonal Antibody DNA Sequencing. Cytoplasmic RNA was extracted from about $10^6$ B7 hybridoma cells as described by Faloro et al (Faloro, J. et al. Methods in Enzimology 65:718–149, (1989).

The cDNA synthesis reaction consisted of 5 ug RNA, 50 mM Tris-HCl, pH 7.5, 75 mM KCl, 10 mM DTT, 3 mM $MgCl_2$, 25 pmol CG2AFOR primer (5'GGAAGCTTAGACCGATGGGGCCTGTTGTTTTG 3') for heavy chain variable region or CK2FOR (5'GGAAGCTTGAAGATGGATACAGTTGGTGCAGC 3') for light chain variable region, 250 uM each of dATP, dTTP, dCTP, dGTP, 15 u ribonuclease inhibitor (RNA guard, Pharmacy) in a total volume of 50 ul. Samples were heated at 70° C., for 10 min. and slowly cooled to 37° C. over a period of 30 min. Then, 100 units MMLV reverse transcriptase (BRL) were added and the incubation at 37° C. continued for 1 hour.

The VH and VK cDNAs were amplified using the PCR as described by Orlandi et al (Orlandi, R. et al. Proc. Natl. Acad. Sci. USA 86:3833–3837, (1989)). For PCR amplification of VH, DNA/primer mixtures consisted of 5 ul cDNA, 25 pmoles CG2A FOR (5'GGAAGCTTAGACCGATGGGGCCTGTTGTTTTG3') and VH1 BACK primers (5'AGGT(G/C)(A/C)A(A/G) CTGCAG(G/C)AGTC(A/T)GG 3'.

For PCR amplification of VK, DNA/primers mixtures consisted of 5 ul cDNA, 25 pmoles of CK2 FOR (5'GGAAGCTTGAAGATGGATACAGTTGGTGCAGC 3') and VK10BACK (5'TTGAATTCCAGTGATGTTTTGATGACCCA 3)'primers. To these mixtures were added 2.5mM each of dATP,dCTP,dTTP,and dGTP, 5 ul constituents of 10× buffer thermolase and 1 unit of Thermolase(IBI) in a final volume of 50 ul. Samples were subjected to 25 thermal cycles at 94° C., 30sec; 50° C., 30sec; 72° C., 1 min.; and a last incubation for 5 min. at 72° C. Amplified VH cDNA were purified on Prep. A Gene purification kit (BioRad).

The purified VH and were cloned into M13 vector. Clones were sequenced by the dideoxy method using T7 DNA Pol (Pharmacy). See FIG. 11.

EXAMPLE 9

Modification of the Variable Domain Sequences Heavy Chain of B7 Murine Monoclonal Antibody to Humanize the Predicted T-cell Antigenic Sequences.

The variable region sequences of heavy of B7 were analyzed for T-cell antigenic sequences. It was made by using the computer algorithm AMPHI, which predict segments of the sequences 11 amino acids in length with an amphipatic helix structure, that is have one side hydrophobic and one side hydrophilic which bind to MHC II molecules.

On to the variable domain sequence of the heavy chain were predicted 3 segments which are: (It is used Kabat's numbering.).

1. FR 1 between amino acids 8–20.
2. FR 1 , CDR 1 and FR2 between amino acids 28–54.
3. FR3, CDR3 and FR4 between amino acids 88–109.

The FIG. 11 shows the sequences corresponding to heavy chain.

This murine sequence is compared with the immunoglobulin sequences included in the Gene Bank and EMBL database. The most homologous human variable region sequence is determined and also the human subgroup to which the murine sequence most closely resembles is defined. In this case the human sequence founded was an TH9 Kabat's subgroup 1.

Both variable region sequences, human and murine are then compared residue by residue and are selected those residues at FR regions which are not involved in the Venire zone or with the canonical structures. Therefore they could be changed by those residues at the same position onto the human sequence.

For the heavy chain of murine B7 we propose 13 replacements:

1. PRO at position 9 by ALA.
2. LEU at position 11 by VAL.
3. VAL at position 12 by LYS.
4. THR at position 16 by ALA.
5. ILE at position 20 by VAL.
6. MET at position 37 by VAL.
7. GLU at position 38 by ARG.
8. SER at position 40 by ALA.
9. HIS at position 41 by PRO.
10. LYS at position 43 by GLN.
11. SER at position 44 by GLY.
12. ILE at position 48 by MET.
13. SER at position 109 by VAL.

EXAMPLE 10

Construction of Mutant Heavy Chain Variable Region of B7 by PCR Mutagenesis.

The changes in the amino acids of mutant heavy chain variable region were constructed using PCR mutagenesis (Kammann, M. et al. Proc. Nat. Aca. Sci, USA, 86, 4220–4224, (1989).

Briefly: Two amplification by PCR: the reaction mixture was: 0.5 ul the VH supernatant of single strand DNA cloned in M13, 25 pmoles mutagenic oligo 1 or 2, 25 pmoles mutagenic oligo 3 or 4 primers (See below the primers sequences). To these mixtures were added 2.5 mM each of dATP, dCTP, dTTP, and dGTP, 5 ul constituents of 10× Vent Polymerase buffer (NEB) and 1 unit of Vent DNA Polymerase (NEB) in a final volume of 50 ul. Samples were subjected to 12–15 thermal cycles at 94° C., 30 sec.; 50° C., 30 sec.; 75° C., 1 min.; and a last incubation for 5 min. at 75° C. The products of both PCRs are joined in a second PCR using the outside primers only (3 and 4). Amplified VH DNA were purified on Prep. A Gene purification kit (Bio Rad).

For the changes in the positions 9, 11, 12, 16 and 20 the primers used, were:

Primer1:
5'CTTGCAGGATACCTTGACTGAAGC-CCCAGGCTTCTTCACCTCAGCTCC 3'.
Primer 3:5'GTAAAACGACGGCCAGT 3'.
These primers are combined in one PCR.
Primer 2:5'GGAGCTGAGGTGAAGAAGCCTGGGGCT-TCAGTCAAGGTATCCTGCAAG3'. Primer 4:5'ACTGGCCGTCGTTTTAC 3'.
These primers are combine in one PCR.
Then, the products of both PCRs are combined in one PCR using 3 and 4 primers.

For the changes in the position 37, 38, 40, 41, 43, 44 and 48, the primers designed were:

Primer 1:
5'AACACCTCCCATCCACTCAAGGCCCT-GTCCAGGGGCCTGCCTCACCCAGTGCAT GGT 3'.
Primer 3:5'GTAAAACGACGGCCAGT 3'.
These primers are combined in one PCR.
Primer2:
5'ATGCACTGGGTGAGGCAGGCCCCTGGA-CAGGGCCTTGAGTGGATGGGAGGT3'. Primer 4: 5'ACTGGCCGTCGTTTTAC 3'.
These primers are combined in one PCR.
Then, the products of both PCRs are combined in one PCR using 3 and 4 primers.

After mutagenesis VH genes were cloned in expression vectors (pSVgpt) yielding the plasmids B7-mut VH-pSVgpt.

BRIEF DESCRIPTION OF THE FIGURES

FIG. 8B shows the positive control, while FIG. 8C shows the negative control (ior r3 Mab, a non-idiotypically connected Mab).

A— Binding of B7 Mab to the human lymphocytes of different normal human donors (B7 Mab at 50 ug/ml).

B— Positive control (CD3 Mab).

C— Negative control (R3 Mab).

Figure 1:
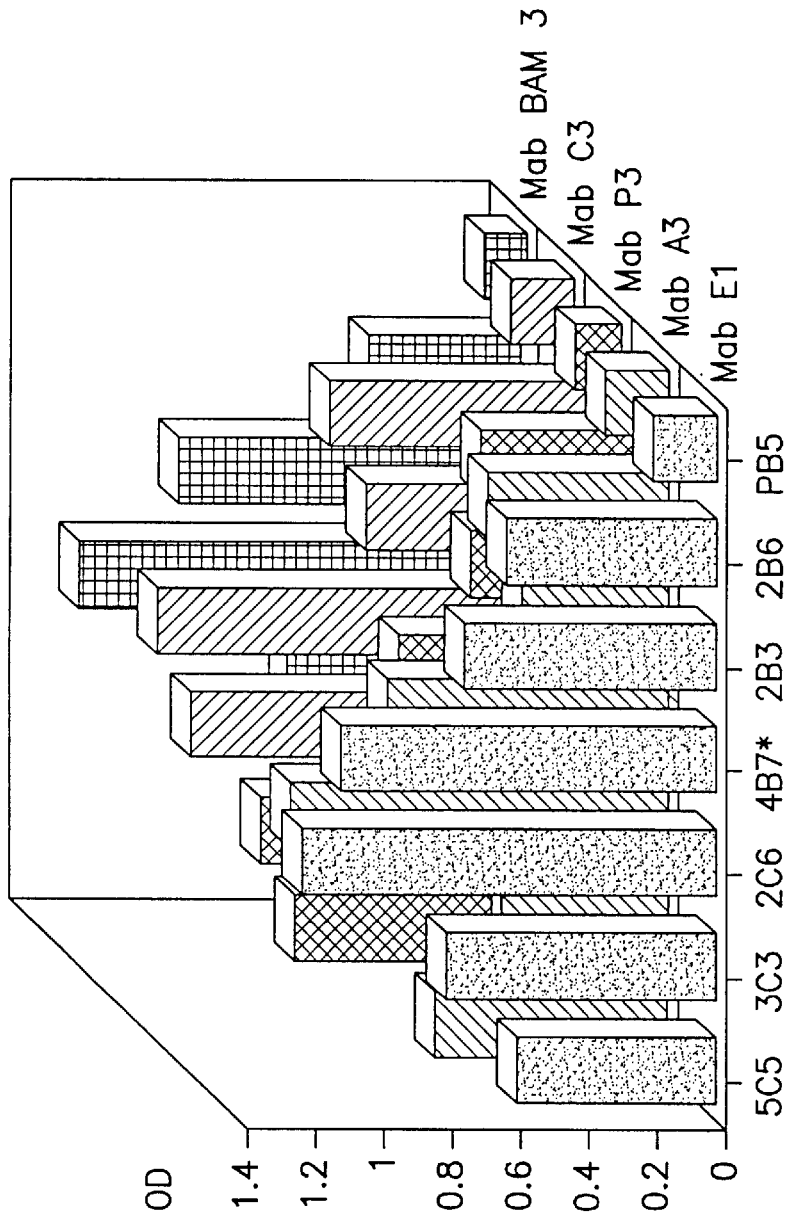
FIG. 1: Show the recognition pattern of the high connected antidiotypic hibridomas with different monoclonals antibodies.
Figure 3:
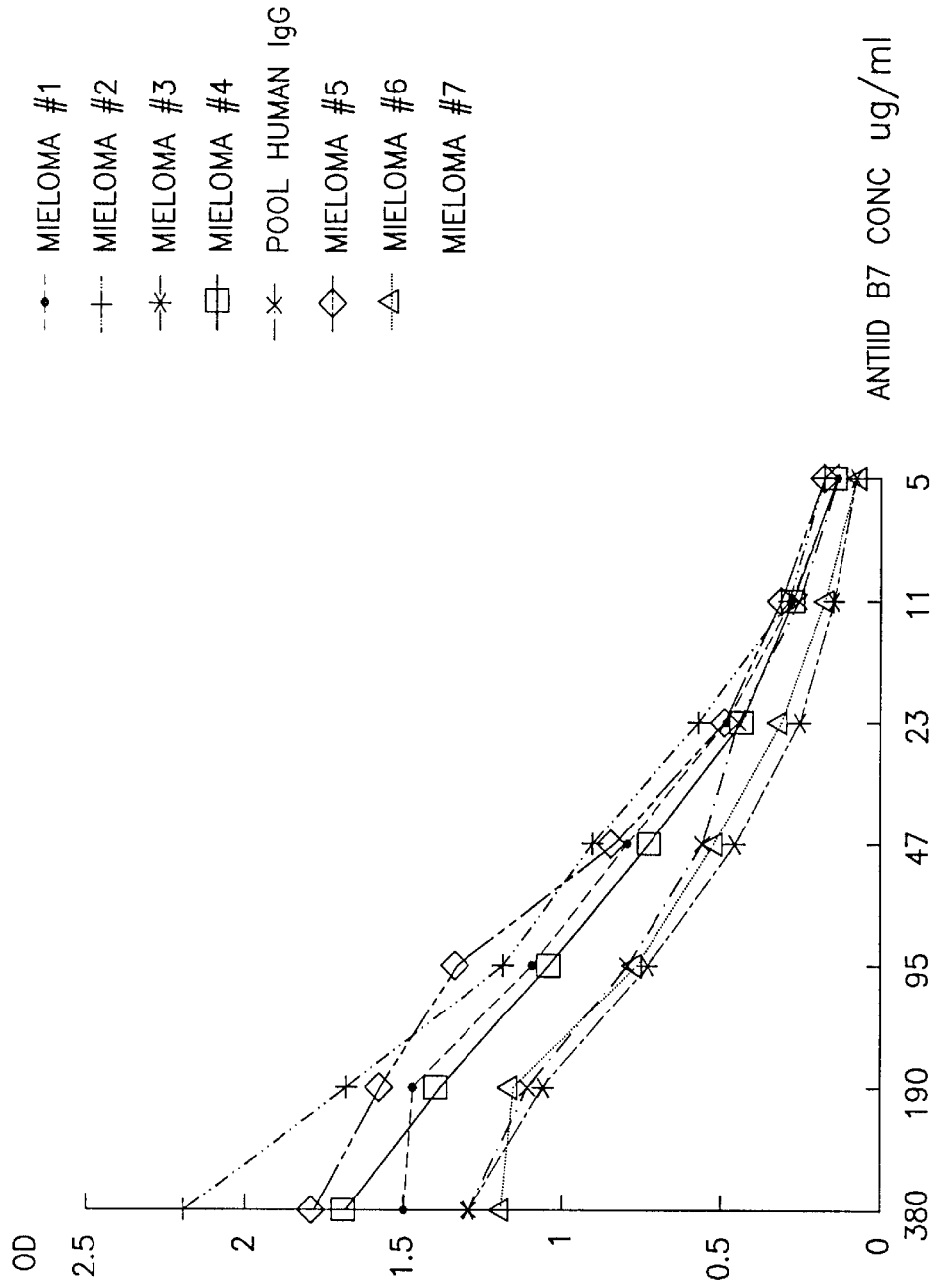
FIG. 3: Show the recognition of different human IgG mieloma proteins and the human intravenous IgG by the B7 Mab.
Figure 4:
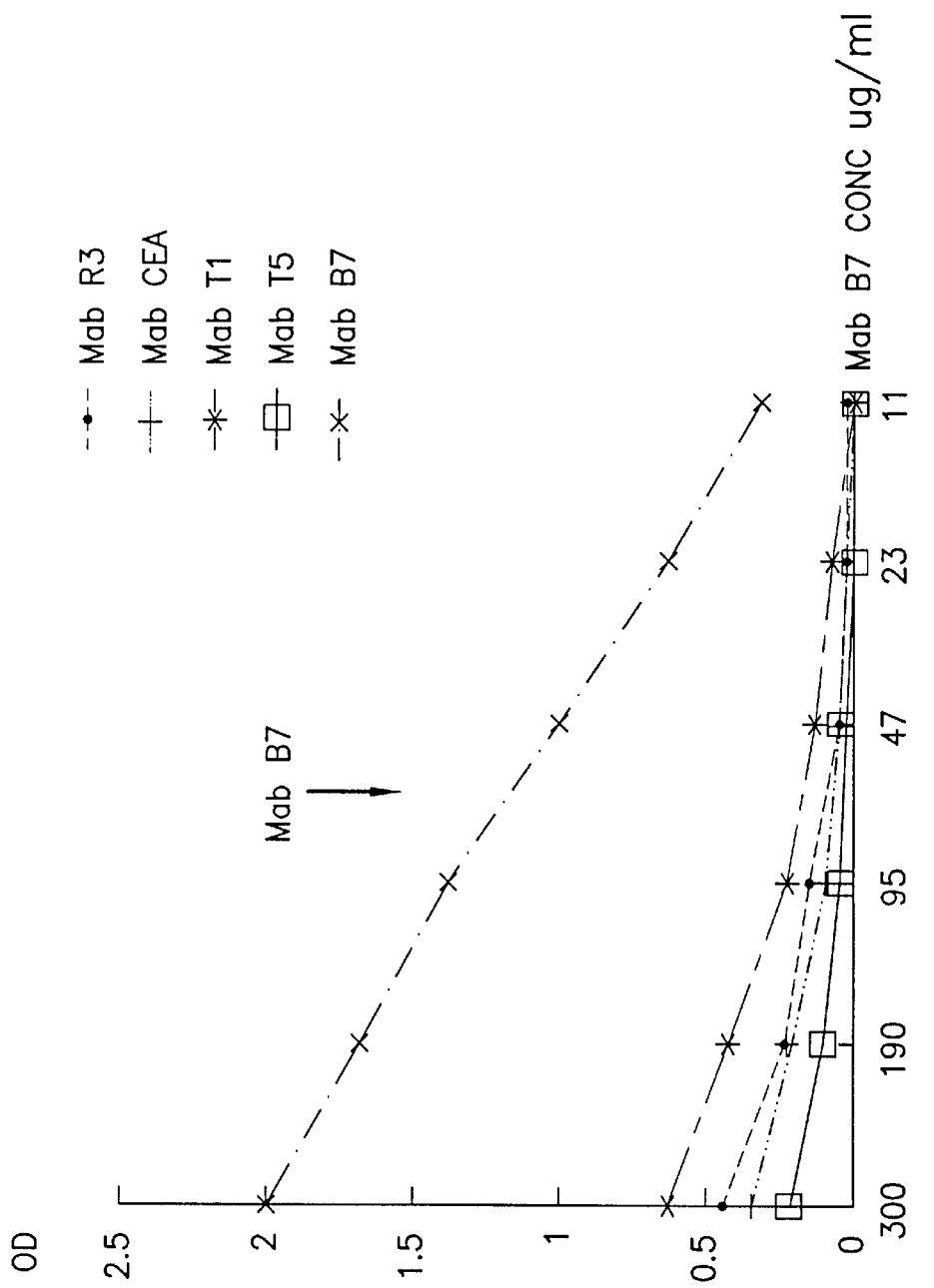
FIG. 4: Show the binding of different murine Mabs by the human mieloma protein #2.
Figure 5:
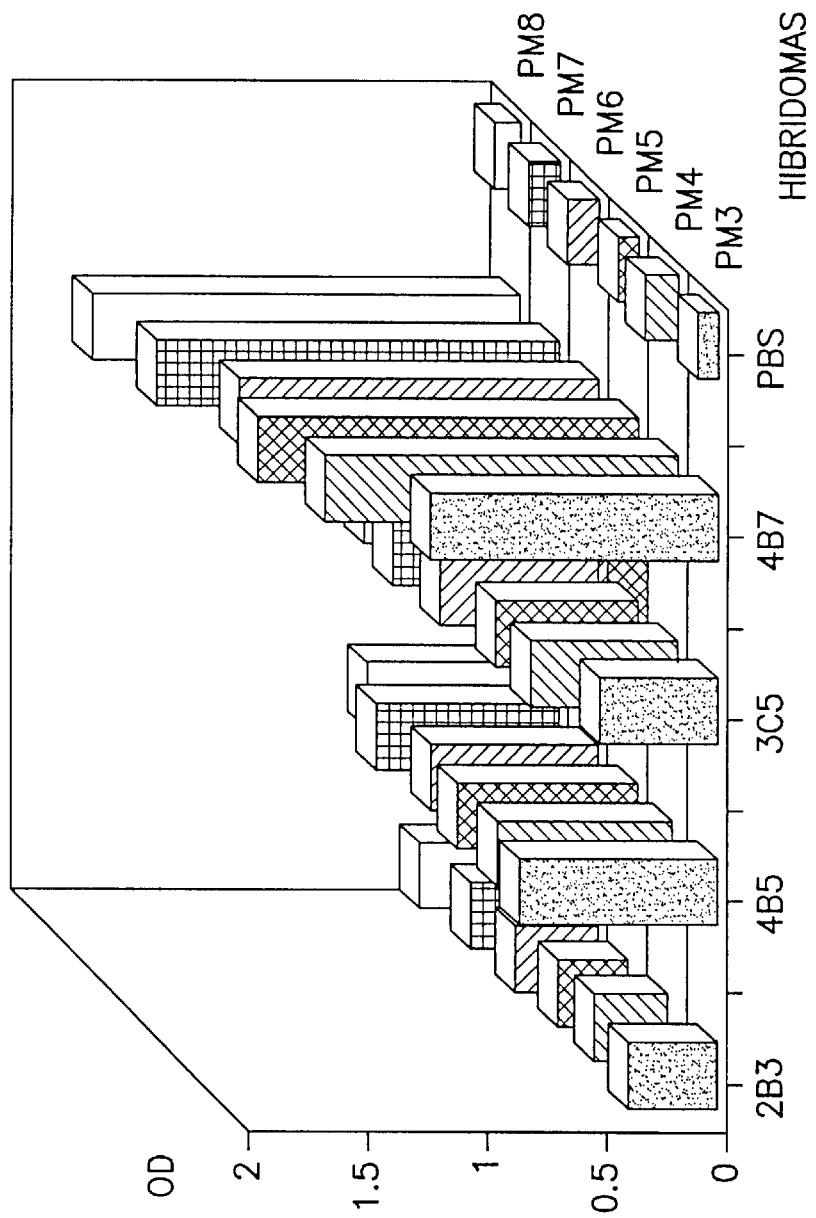
FIG. 5: Show the recognition pattern of the IgG high connected antidiotypics Mabs by differents IgG human mieloma proteins.
Figure 6:
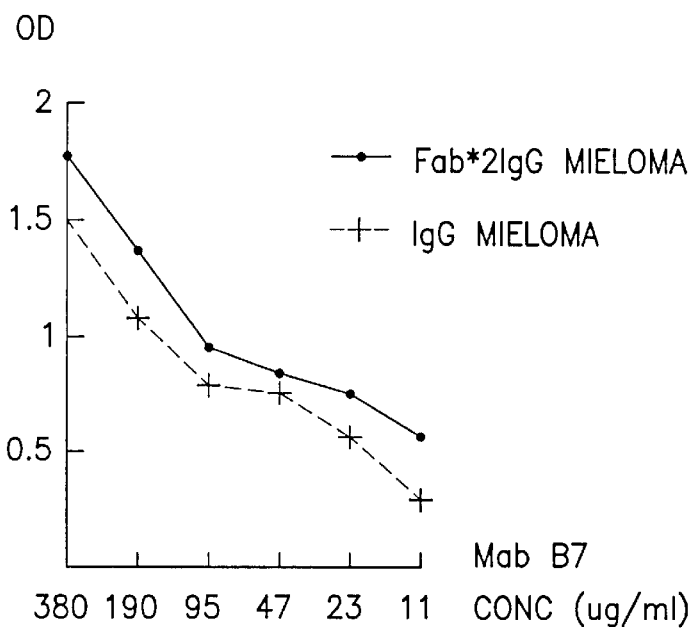
FIG. 6: Show the binding of undigested IgG human mieloma and their Fab'2 by the B7 Mabs.
Figure 7:
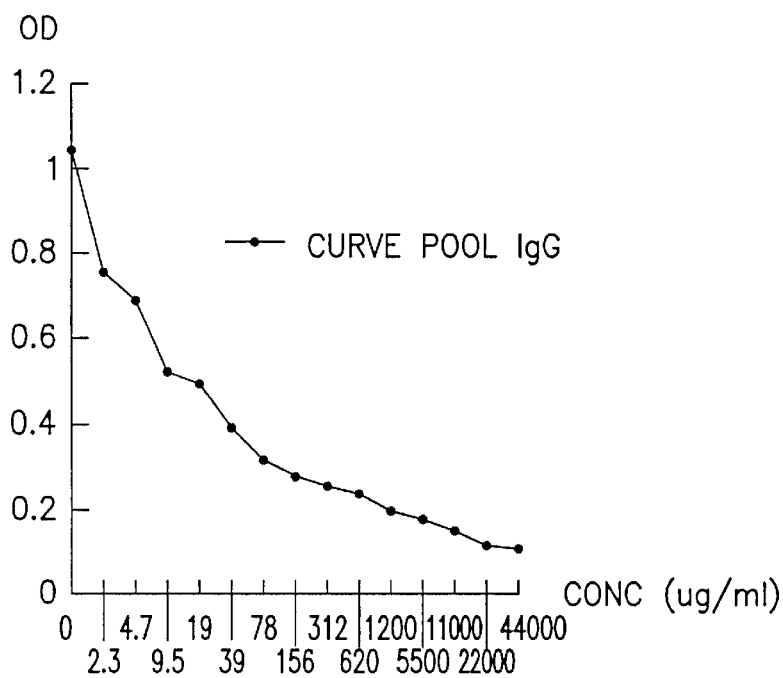
FIG. 7: Show the competitive inhibition by the intravenous human IgG of the B7 Mab binding to the human IgG mieloma protein.
Figures 2, 8A:
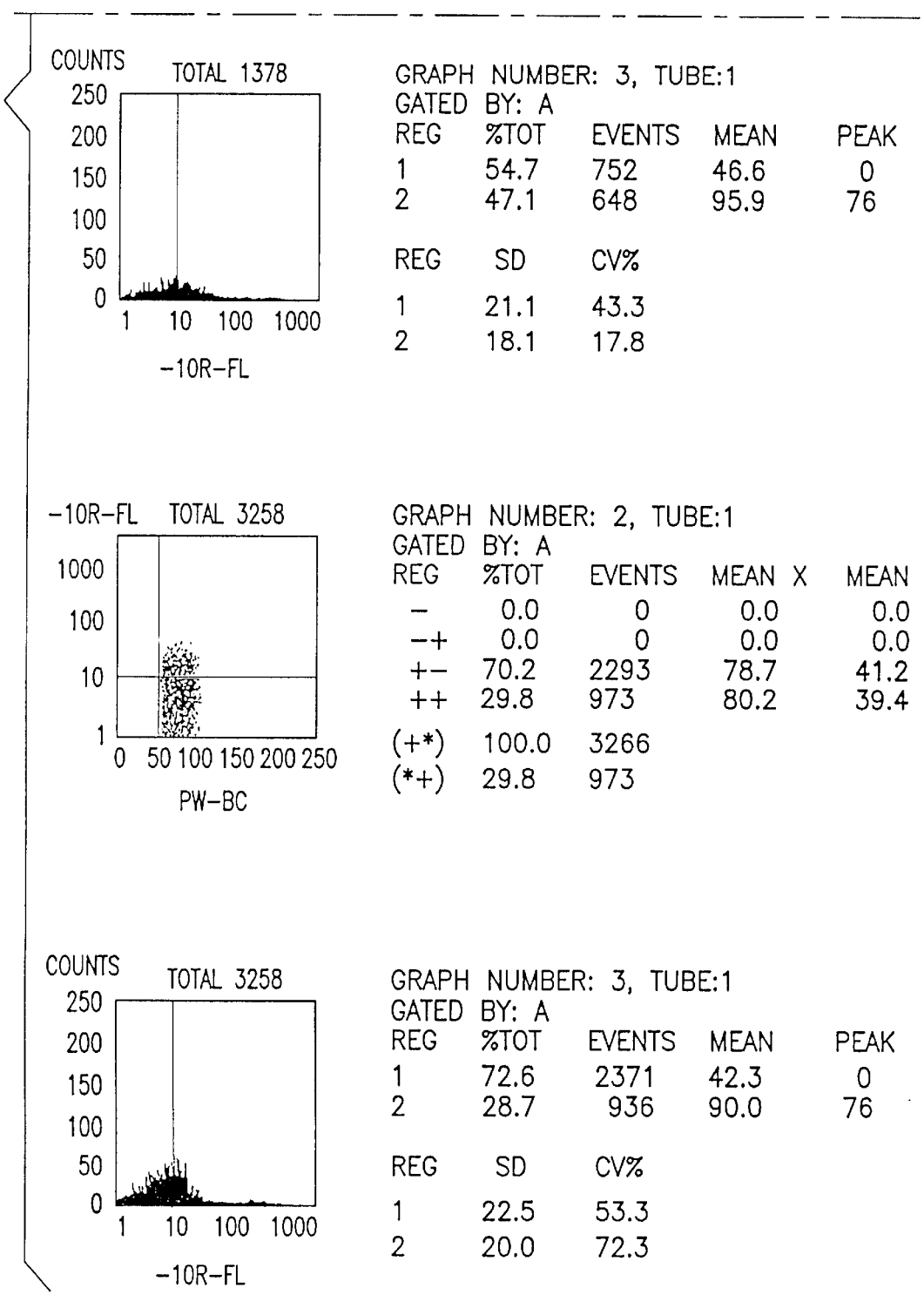
FIG. 2: Show the binding of the B7 Mab to different monoclonal antibodies.
FIG. 8A shows the recognition analysis of human B and T lymphocytes by the B7 Mab in the flow cytometer.
Figure 9A:
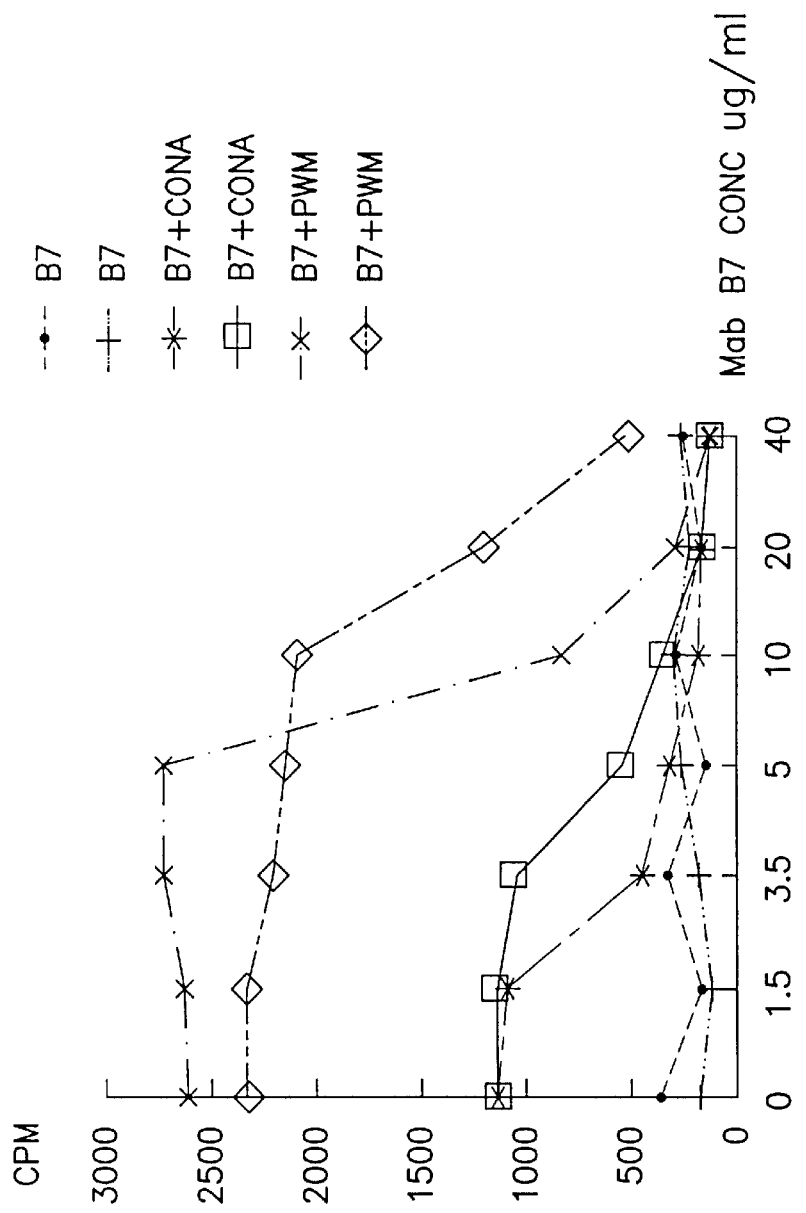

FIGS. 9A–B: Show the effect of the B7 Mab on human lymphocytes proliferative responses to CONA,PWM and PHA.

A— Human lymphocytes +CONA and PWM.

B— Human lymphocytes +PHA.

Figure 10A:
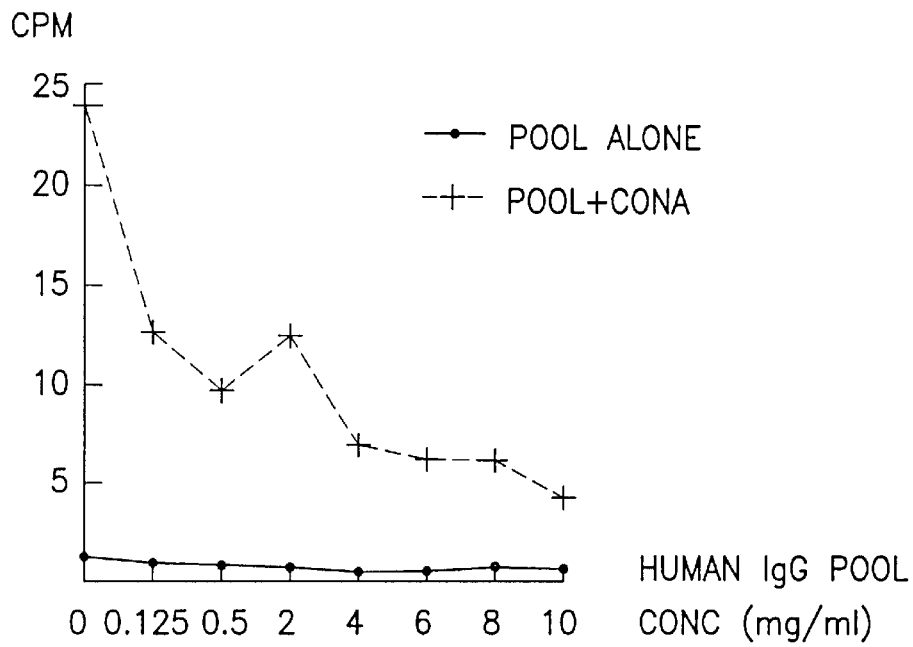
Figure 10B:
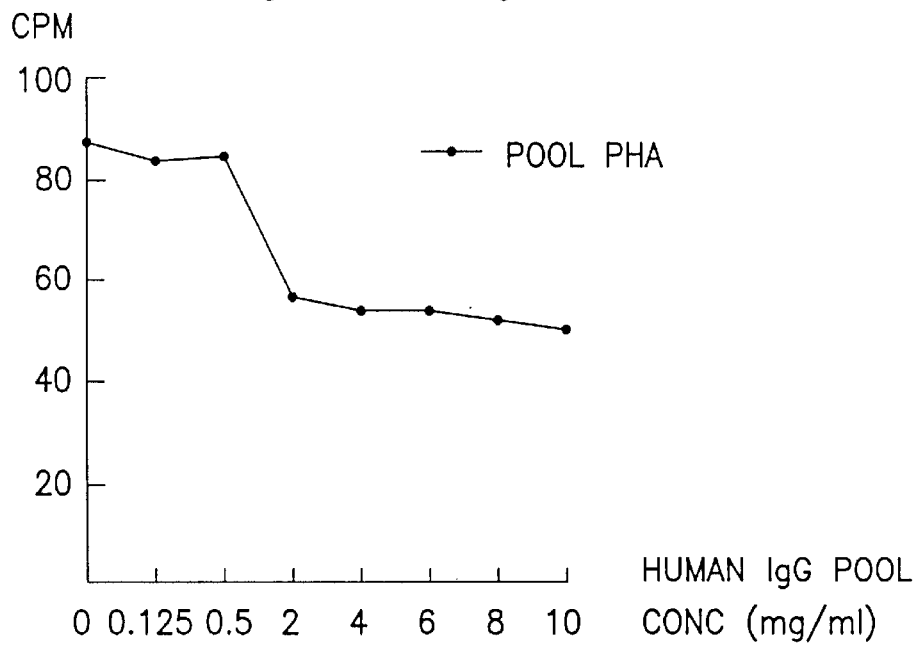

FIGS. 10A–B: Show the effect of the human intravenous IgG on human lymphocyte proliferate responses to CONA and PHA.

Results are expressed as the mean cpm of triplicate values from three independent experiments.

A— iv IgG alone +iv IgG and CONA.

B— iv IgG+PHA.

FIG. 11: Analysis for the modification by way of humanization of the variable regions of the heavy chain of antibody B7.

A: Sequence of the variable region of the murine B7 monoclonal antibody.

B: Sequence of the variable region of the most homologous human immunoglobulin.

C: Sequence of the modified variable region of B7.

Shading: predicted T-cell antigenic sequences.

Underlined amino acids residues: amino acids involved in tertiary structure.

Bold font: complementarity determining regions.

Amino acids residues in boxes: replacements which are proposed.

What is claimed is:

1. An IgG antibody that is useful as an immunoregulator of the immune response, which is a humanized variant of murine monoclonal antibody B7 produced by hybridoma E.C.A.C.C. 94113024, wherein the heavy chain of said IgG antibody comprises a constant region of a human immunogloblin and a variable region with amino acid sequence:

(SEQ ID NO:1)

```
GLN VAL GLN LEU GLN GLN SER GLY ALA GLU VAL LYS

LYS PRO GLY ALA SER VAL LYS VAL SER CYS LYS THR

SER GLY TYR THR PHE THY GLU TYR THR MET HIS TRP

VAL ARG GLN ALA PRO GLY GLN GLY LEU GLU TRP MET

GLY GLY VAL SER PRO ASN ASN GLY GLY ALA SER TYR

ASN GLN LYS PHE LYS GLY LYS ALA THR LEU THR VAL

ASP LYS SER SER ASN THR ALA TYR MET GLU LEU ARG

SER LEU THR SER ASP ASP SER ALA VAL TYR TYR CYS

ALA ARG ARG LEU GLY ARG GLY TYR ASP LEU ALA SER

TYR TRP GLY GLN GLY THR LEU VAL LEU SER LEU GLN.
```

\* \* \* \* \*

```
                          SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
        (A) LENGTH: 120 Amino acid residues
        (B) TYPE: Amino acid
        (C) STRANDEDNESS: Unknown
        (D) TOPOLOGY: Unknown (ii) MOLECULE TYPE: Protein (iii) HYPOTHETICAL: No (iv) ANTI-SENSE: No (v) FRAGMENT TYPE: -N Terminal fragment.

(vi) ORIGINAL SOURCE:
        (A) ORGANISM: Mice Balb/C
        (F) TISSUE TYPE:  Murine hibridoma (vii) IMMEDIATE SOURCE:
        (B) CLONE: B7

(ix) FEATURE:
        (C) IDENTIFICATION METHOD: Experimental.
        (D) OTHER INFORMATION:  - Sequence corresponding to the
            variable region of its heavy chain of the humanized
            variant obtained from the monoclonal antibody B7.

(xi) SEQUENCE DESCRIPTION: SEQ ID NO: 1:

Gln Val Gln Leu Gln Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
                20                  25                  30

Thr Met His Trp Val Arg Gln Ala Pro Gly Gln Gly Leu Glu Trp Met
            35                  40                  45

Gly Gly Val Ser Pro Asn Asn Gly Gly Ala Ser Tyr Asn Gln Lys Phe
    50                  55                  60

Lys Gly Lys Ala Thr Leu Thr Val Asp Lys Ser Ser Asn Thr Ala Tyr
65                  70                  75                  80

Met Glu Leu Arg Ser Leu Thr Ser Asp Asp Ser Ala Val Tyr Tyr Cys
                85                  90                  95
```

-continued

```
Ala Arg Arg Leu Gly Arg Gly Tyr Asp Leu Ala Ser Tyr Trp Gly Gln
            100                 105                 110

Gly Thr Leu Val Leu Ser Leu Gln
        115             120
```